US012533670B2

(12) United States Patent
Xu et al.

(10) Patent No.: US 12,533,670 B2
(45) Date of Patent: Jan. 27, 2026

(54) MICROFLUIDIC SUBSTRATE AND MANUFACTURING METHOD THEREFOR, AND MICROFLUIDIC CHIP

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Shanshan Xu, Beijing (CN); Zhao Chen, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 1222 days.

(21) Appl. No.: 17/040,311

(22) PCT Filed: Dec. 13, 2019

(86) PCT No.: PCT/CN2019/125198
§ 371 (c)(1),
(2) Date: Sep. 22, 2020

(87) PCT Pub. No.: WO2020/140732
PCT Pub. Date: Jul. 9, 2020

(65) Prior Publication Data

US 2021/0086181 A1 Mar. 25, 2021

(30) Foreign Application Priority Data

Jan. 3, 2019 (CN) ........................ 201910005343.X

(51) Int. Cl.
*B01L 3/00* (2006.01)
*C12Q 1/6869* (2018.01)

(52) U.S. Cl.
CPC ... *B01L 3/502715* (2013.01); *B01L 3/502784* (2013.01); *C12Q 1/6869* (2013.01); *B01L 2200/12* (2013.01); *B01L 2300/12* (2013.01)

(58) Field of Classification Search
CPC ................................................ B01L 3/502715
See application file for complete search history.

(56) References Cited

U.S. PATENT DOCUMENTS

| | | | | |
|---|---|---|---|---|
| 2007/0225800 | A1* | 9/2007 | Sahatjian | A61F 2/91 623/1.42 |
| 2009/0075838 | A1 | 3/2009 | El Gamal et al. | |
| 2009/0127123 | A1* | 5/2009 | Raccurt | G02B 3/14 205/334 |
| 2013/0050807 | A1 | 2/2013 | Lee et al. | |
| 2016/0184823 | A1 | 6/2016 | Fischer | |

FOREIGN PATENT DOCUMENTS

| | | | |
|---|---|---|---|
| CN | 102500436 | A | 6/2012 |
| CN | 104388299 | A | 3/2015 |
| CN | 106291911 | A | 1/2017 |
| CN | 106540762 | A | 3/2017 |
| CN | 106770294 | A | 5/2017 |
| CN | 107754962 | A | 3/2018 |
| CN | 109092379 | A | 12/2018 |
| CN | 109652287 | A | 4/2019 |

OTHER PUBLICATIONS

D. Orejon et al., Young-Lippmann Equation Revisited for Nano-Suspensions, 102 Appl. Phys. Lett. 201601 (2013).*
Office Action dated Apr. 7, 2020 in counterpart CN Patent Application No. 201910005343.X, 13 pages.
Office Action dated Dec. 24, 2020 in counterpart CN Patent Application No. 201910005343.X, 10 pages.

* cited by examiner

*Primary Examiner* — Randy Boyer
(74) *Attorney, Agent, or Firm* — Procopio, Cory, Hargreaves & Savitch LLP

(57) ABSTRACT

A microfluidic substrate includes an electrode substrate and a dielectric layer disposed on a side of the electrode substrate. The dielectric layer includes a dielectric material, and a molecular structure of the dielectric material has a hydrophobic group.

12 Claims, 7 Drawing Sheets

MICROFLUIDIC SUBSTRATE AND MANUFACTURING METHOD THEREFOR, AND MICROFLUIDIC CHIP

CROSS-REFERENCE TO RELATED APPLICATIONS

This application is a national phase entry under 35 USC 371 of International Patent Application No. PCT/CN2019/125198 filed on Dec. 13, 2019, which claims priority to Chinese Patent Application No. 201910005343.X, filed on Jan. 3, 2019, which are incorporated herein by reference in their entirety.

TECHNICAL FIELD

The present disclosure relates to the field of gene sequencing technologies, and in particular, to a microfluidic substrate and a method for manufacturing the same, and a microfluidic chip.

BACKGROUND

Gene sequencing is an important means for determining sequence of bases of a target DNA and performing various related analyses, and thus may enable researchers to study organisms at a molecular biological level.

In a process of gene sequencing, a digital microfluidic biochip (abbreviated as DMFB) is generally used to study and analyze genes. The existing digital microfluidic biochip can control a test liquid by utilizing a microfluidic substrate, so as to realize detection of the test liquid.

SUMMARY

In one aspect, a microfluidic substrate is provided. The microfluidic substrate includes an electrode substrate and a dielectric layer disposed on a side of the electrode substrate. The dielectric layer includes a dielectric material, and a molecular structure of the dielectric material has a hydrophobic group.

In some embodiments, the dielectric layer includes a base layer and a plurality of columnar structures disposed on a surface of the base layer away from the electrode substrate.

In some embodiments, the dielectric layer further includes a plurality of roughened structures, at least one roughened structure of the plurality of roughened structures is disposed on a columnar surface of each columnar structure of the plurality of columnar structures. The at least one roughened structure extends from an end of the columnar structure away from the base layer toward an end of the columnar structure adjacent to the base layer, and a dimension of the at least one roughened structure in an axial direction of the columnar structure is less than or equal to an axial length of the columnar structure.

In some embodiments, the dimension of the at least one roughened structure in the axial direction of the columnar structure is 0.25 times to 0.5 times the axial dimension of the columnar structure; and/or, a dimension of the at least one roughened structure in a radial direction of the columnar structure is 0.06 times to 0.1 times the axial dimension of the columnar structure.

In some embodiments, the at least one roughened structure includes multiple roughened structures, and the multiple roughened structures are arranged in a circumferential direction of the columnar structure where the at least one roughened structure is located.

In some embodiments, in orthographic projections of the multiple roughened structures on the base layer and an orthographic projection of the columnar structure where the multiple roughened structures are located on the base layer, an edge per micrometre of an orthographic projection of an end face of the columnar structure away from the base layer is connected to orthographic projections of 16 to 32 roughened structures.

In some embodiments, the at least one roughened structure of the plurality of roughened structures is a protrusion disposed on the columnar surface of the columnar structure where the at least one roughened structure is located; and/or, the at least one roughened structure of the plurality of roughened structures is a groove disposed in the columnar surface of the columnar structure where the at least one roughened structure is located.

In some embodiments, the plurality of columnar structures are arranged in at least one manner of: the plurality of columnar structures being evenly distributed on a surface of the base layer; an orthographic projection of the at least one columnar structure of the plurality of columnar structures on the base layer being an orthographic projection at a micron scale; $1\times10^{12}$ to $3\times10^{12}$ columnar structures being disposed on the surface of the base layer per square meter; a radial dimension of a columnar structure being greater than or equal to a distance between two adjacent columnar structures; the radial dimension of the columnar structure being less than or equal to an axial dimension of the columnar structure; an area of an end face of the columnar structure adjacent to the base layer being greater than or equal to an area of an end face of the columnar structure away from the base layer; a shape of the columnar structure being a conical frustum shape or a cylinder; an orthographic projection of the end face of the columnar structure away from the base layer on the base layer being a circular projection; or the end face of the columnar structure away from the base layer being parallel to the base layer.

In some embodiments, a thickness of the dielectric layer is:

$$d = \frac{V^2\varepsilon_0\varepsilon}{2\gamma_{LG}(\cos\theta - \cos\theta_0)};$$

Wherein V is a voltage applied to the electrode substrate, to is a vacuum dielectric constant, ε is a dielectric constant of the dielectric material included in the dielectric layer, $\theta_0$ is an initial contact angle of a test liquid on the dielectric layer, θ is a contact angle of the test liquid on the dielectric layer under action of the applied voltage, and $\gamma_{LG}$ is a surface tension of the test liquid at a gas-liquid interface at 25° C.

In some embodiments, a dielectric constant of the dielectric material included in the dielectric layer is 2 to 8.

In some embodiments, the dielectric material includes at least one of polydimethylsiloxane, polymethyl methacrylate or fluorosilicone rubber.

In some embodiments, the hydrophobic group includes at least one of an alkyl group, an ester group or a halogen.

In some embodiments, the electrode substrate includes abase substrate and an electrode layer disposed between the base substrate and the dielectric layer. The electrode layer includes a plurality of driving electrodes arranged in an array, or the electrode layer includes a whole layer of reference electrode.

In another aspect, a method for manufacturing a microfluidic substrate is provided. The method includes: manufacturing an electrode substrate; forming a dielectric layer on a side of the electrode substrate, a molecular structure of a dielectric material included in the dielectric layer has a hydrophobic groups.

In some embodiments, the dielectric layer includes a base layer and a plurality of columnar structures disposed on a surface of the base layer away from the electrode substrate. Forming the dielectric layer on the side of the electrode substrate includes: providing a template, the template including a template body and a plurality of depressions formed in the template body; providing the dielectric material on a surface of the template body with the plurality of depressions and in the plurality of depressions; curing the dielectric material to obtain the dielectric layer in contact with the surface of the template body and inner walls of the plurality of depressions; and detaching the dielectric layer from the template.

In some embodiments, providing the dielectric material on the surface of the template body with the plurality of depressions and in the plurality of depressions, includes: coating the dielectric material on the surface of the template body with the plurality of depressions; providing the electrode substrate on a side of the template body coated with the dielectric material, the electrode substrate including a base substrate and an electrode layer disposed on a side of the base substrate, and the electrode layer being in contact with the dielectric material; and pressing the electrode substrate by using a pressing roller, to make the dielectric material coated on the surface of the template body enter the plurality of depressions under action of the electrode substrate.

In some embodiments, a plurality of microstructures are formed in an inner side wall of at least one depression of the plurality of depressions, and at least one microstructure of the plurality of microstructures is a protrusion or a groove.

In some embodiments, the plurality of microstructures are formed in a circumferential direction of the inner side wall of a depression where the plurality of microstructures are located.

In yet another aspect, a microfluidic chip is provided. The microfluidic chip includes a first microfluidic substrate and a second microfluidic substrate that are disposed opposite to each other. At least one of the first microfluidic substrate and the second microfluidic substrate is the microfluidic substrate as provided in any of the above embodiments. An accommodation space for receiving a test liquid is formed between the first microfluidic substrate and the second microfluidic substrate.

BRIEF DESCRIPTION OF THE DRAWINGS

In order to describe technical solutions in the present disclosure more clearly, accompanying drawings to be used in some embodiments of the present disclosure will be introduced below briefly. Obviously, the accompanying drawings to be described below are merely accompanying drawings of some embodiments of the present disclosure, and a person of ordinary skill in the art can obtain other drawings according to these drawings. In addition, the accompanying drawings to be described below may be regarded as schematic diagrams, and are not limitations on actual sizes of products and actual processes of methods that the embodiments of the present disclosure relate to.

DETAILED DESCRIPTION

Technical solutions in some embodiments of the present disclosure will be described clearly and completely in combination with accompanying drawings. Obviously, the described embodiments are merely some but not all embodiments of the present disclosure. All other embodiments obtained on a basis of the embodiments of the present disclosure by a person of ordinary skill in the art shall be included in the protection scope of the present disclosure.

Terms such as “first” and “second” are used for descriptive purposes only, and are not to be construed as indicating or implying the relative importance or implicitly indicating the number of indicated technical features below. Thus, features defined as “first” and “second” may explicitly or implicitly include one or more of the features. In the description of the embodiments of the present disclosure, the term “a plurality of” and “the plurality of” mean two or more unless otherwise specified.

"At least one of A. B and C" has a same meaning as "at least one of A, B or C", and they both include the following combinations of A, B and C: only A, only B, only C, a combination of A and B, a combination of A and C, a combination of B and C, and a combination of A, B and C. "A and/or B" includes the following three combinations: only A, only B, and a combination of A and B.

A gene, also known as a genetic factor, refers to a DNA or RNA sequence that carries genetic information, which is a basic genetic unit for controlling a trait. The gene expresses the genetic information carried by itself by guiding synthesis of proteins, thereby controlling trait performance of individual organisms. The gene has functions to control a genetic trait and to adjust an activity. The gene passes genetic information to next generation through replication, and controls metabolic processes by controlling synthesis of enzymes, thereby controlling trait performance of individual organisms. The gene can also directly control biological trait by controlling composition of structural proteins. Therefore, gene sequencing is generally used to study and analyze genes in modern biological research.

Gene sequencing is a novel gene detection technology, which can analyze and determine a complete sequence of genes from blood or saliva to predict the potential for suffering from various diseases, individual behavioral characteristics and rationality of behavior. Gene sequencing technology can target individual pathological genes for previous prevention and treatment. Gene sequencing can determine sequence of bases of a target DNA and perform various related analyses, and thus is one of the important research means of modern biology, and is also an important motive force for promoting rapid development of biology.

Figure 1:
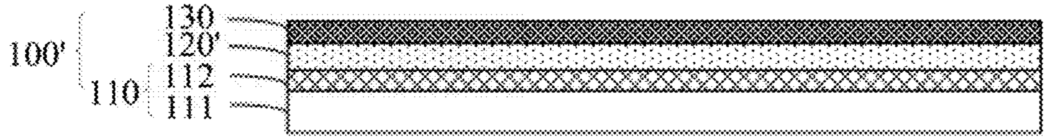
FIG. 1 is a structural diagram of a microfluidic substrate in the related art.

In a process of gene sequencing, a digital microfluidic biochip (abbreviated as DMFB) is generally used to study and analyze genes. The DMFB has a good application prospect in fields such as biology, medicine, chemistry and detection due to advantages of small amount of reagent, configurable, concurrent processing and easy automation. The digital microfluidic biochip can control a test liquid by utilizing a microfluidic substrate, so as to realize detection of the test liquid. Referring to FIG. 1, a microfluidic substrate 100' in the related art includes an electrode substrate 110, a dielectric film 120' and a hydrophobic layer 130 that are sequentially stacked. The hydrophobic layer 130 is used to be in contact with the test liquid, so that a certain contact angle is formed between the test liquid and the microfluidic substrate 100', and thus the movement of the test liquid may be controlled by the microfluidic substrate 100'. The dielectric film 120' may prevent the microfluidic substrate 100' from being broken down during energization, so as to ensure that the microfluidic substrate 100' may control the test liquid.

In a process of manufacturing the microfluidic substrate 100', the dielectric film 120' and the hydrophobic layer 130 are sequentially formed on the electrode substrate 110. However, after the dielectric film 120' is formed on the electrode substrate 110, if a foreign object with high hardness is attached to a surface of the dielectric film 120' away from the electrode layer 112, the foreign object with high hardness is prone to pierce the dielectric thin film 120' after the hydrophobic layer 130 is provided, resulting in a failure of dielectric effect of the dielectric film 120', so that the microfluidic substrate 100' may not work normally. Therefore, the production yield of the microfluidic substrate 100' in the related art is relatively low. In addition, the hydrophobic layer 130 of the microfluidic substrate 100' in the related art has a low surface energy due to a hydrophobic material, which makes poor adhesion between the hydrophobic layer 130 and the dielectric film 120'.

Figure 2:
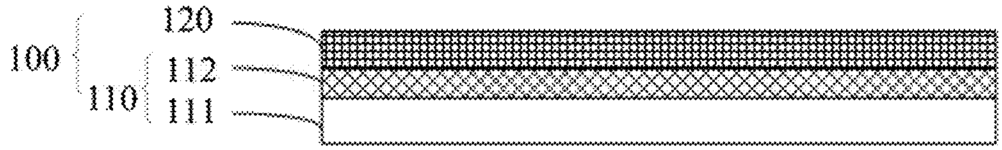
FIG. 2 is a structural diagram of a microfluidic substrate, in accordance with some embodiments of the present disclosure.

Some embodiments of the present disclosure provide a microfluidic substrate. As shown in FIG. 2, the microfluidic substrate 100 includes an electrode substrate 110 and a dielectric layer 120 disposed on a side of the electrode substrate 110. For example, the electrode substrate 110 includes a base substrate 111 and an electrode layer 112 disposed on the base substrate, and the electrode layer 112 is disposed between the dielectric layer 120 and the base substrate 111. It will be noted that the electrode layer 112 may be designed according to needs. For example, the electrode layer 112 includes a whole layer of reference electrode. For another example, the electrode layer 112 includes a plurality of driving electrodes arranged in an array. In this case, a plurality of driving electrodes independent of each other constitute a driving electrode layer.

The dielectric layer 120 includes a dielectric material, and a molecular structure of the dielectric material has a hydrophobic group. For example, the hydrophobic group includes, but is not limited to at least one of an alkyl group, an ester group or a halogen.

In this way, the dielectric layer 120 has both a dielectric function and a certain hydrophobic function. Therefore, in the process of manufacturing the microfluidic substrate 100, there is no need to form the hydrophobic layer 130 on a surface of the dielectric layer 120 away from the electrode substrate 110, which not only simplifies the structure and manufacturing process of the microfluidic substrate 100, thereby improving production efficiency, but also reduces the probability of a foreign object piercing the dielectric layer 120, thereby improving the production yield of the microfluidic substrate 100.

In addition, since the dielectric layer 120 in the microfluidic substrate 100 has functions of dielectricity and hydrophobicity, the dielectric layer 120 may be used as both a hydrophobic layer and a dielectric layer, so that the problem of poor adhesion between the hydrophobic layer and the dielectric layer included in the existing microfluidic substrate may be solved.

Figure 3:
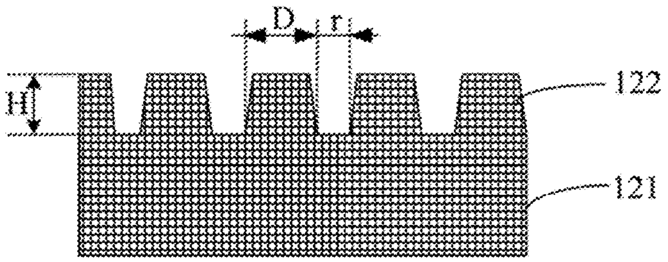
FIG. 3 is a structural diagram of a dielectric layer, in accordance with some embodiments of the present disclosure.

In some embodiments, referring to FIG. 3, the dielectric layer 120 includes a base layer 121 and a plurality of columnar structures 122 disposed on a surface of the base layer 121 away from the electrode substrate. The plurality of columnar structures 122 may constitute a specific surface area adjustment unit. That is, the greater the number of the columnar structures 122 is, the larger a specific surface area of the dielectric layer is, which is more beneficial to reducing a surface energy of the dielectric layer and improving a hydrophobic ability. In other words, the plurality of columnar structures 122 may increase a contact area between the test liquid and the dielectric layer 120 per unit area. The larger the contact area between the test liquid and the dielectric layer 120 per unit area is, the better the hydrophobic performance of the dielectric layer 120 is. Therefore, the number of the columnar structures 122 disposed on the base layer 121 is controlled such that the dielectric layer 120 meets the hydrophobic requirements of the microfluidic substrate 100 for the test liquid. Furthermore, this design may make a contact angle between the dielectric layer 120 and the test liquid (e.g., water) reach 135° after tests, so as to have good hydrophobic performance.

In order to enable the microfluidic substrate 100 to control the movement of the test liquid, in some embodiments, a thickness of the dielectric layer 120 is d:

$$d = \frac{V^2 \varepsilon_0 \varepsilon}{2\gamma_{LG}(\cos\theta - \cos\theta_0)};$$

where V is a voltage applied to the electrode substrate (i.e., a voltage applied to the electrode layer included in the electrode substrate; it will be understood that in a case where the electrode layer includes a plurality of driving electrodes, the voltage is a driving voltage; and in a case where the electrode layer includes a whole layer of reference electrode, the voltage may be a reference voltage equal to the driving voltage). $\varepsilon_0$ is a vacuum dielectric constant, ε is a dielectric constant of the dielectric material included in the dielectric layer 120, $\theta_0$ is an initial contact angle of the test liquid on the dielectric layer 120 (i.e., a contact angle of the test liquid on the base layer 121 included in the dielectric layer 120 without applying a voltage), θ is a contact angle of the test liquid on the dielectric layer 120 under action of the driving voltage (i.e., a contact angle of the test liquid on the base layer 121 included in the dielectric layer 120 under action of the driving voltage), and $\gamma_{LG}$ is a surface tension of the test liquid at a gas-liquid interface at 25° C.

For example, in a case where the test liquid is water and the dielectric material is polydimethylsiloxane, $\varepsilon_0$=8.854×$10^{-12}$ F/m, ε=2.8, $\theta_0$=112°, θ=90, $\gamma_{LG}$=0.07 N/m, d=3.5416×$10^{-10}$×$V^2$.

It can be understood that the thickness of the dielectric layer 120 refers to a sum of a height of the columnar structure and a thickness of the base layer, and a height direction of the columnar structure is the same as a thickness direction of the base layer.

It will be noted that the dielectric constant of the dielectric material included in the dielectric layer 120 may be selected according to actual needs. For example, the dielectric constant of the dielectric material included in the dielectric layer 120 is within a range from 2 to 8, for example, 2 to 4, 4 to 6 or 6 to 8. Within this range, the dielectric layer 120 may not only have good hydrophobic performance, but also effectively prevent the electrode layer from being broken down.

The dielectric material included in the dielectric layer 120 is various, and is not limited to polydimethylsiloxane. For example, the dielectric material included in the dielectric layer 120 may be at least one of polydimethylsiloxane, polymethyl methacrylate or fluorosilicone rubber.

In some embodiments, as shown in FIGS. 3 to 9, the plurality of columnar structures 122 included in the dielectric layer 120 may constitute a micro-nano structure. That is, an orthographic projection of each columnar structure 122 on a plane where the base layer 121 is located is an orthographic projection at the micron scale (e.g., 1 μm to 10 μm), so that the specific surface area of the dielectric layer 120 is larger. Therefore, in the microfluidic substrate 100 provided in some embodiments of the present disclosure, the contact area between the dielectric layer 120 per unit area and the test liquid is larger, and the dielectric layer 120 per unit area has more hydrophobic groups which are in contact with the test liquid, so that the dielectric layer 120 has a better hydrophobic performance.

It can be understood that since the molecular structure of the dielectric material included in the dielectric layer 120 has hydrophobic group(s), and the dielectric layer 120 includes the base layer 121 and the plurality of columnar structures 122, all the base layer 121 and the plurality of columnar structures 122 have certain hydrophobicity.

Figure 11:
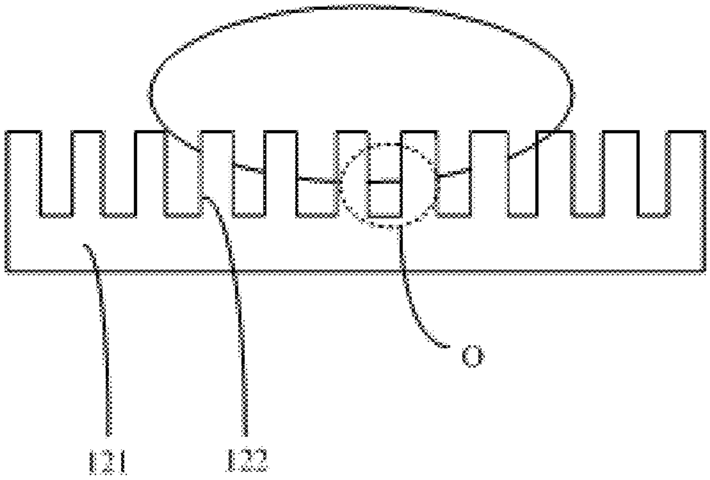
FIG. 11 is a view of a gas-liquid-solid three-phase system, in accordance with some embodiments of the present disclosure.

Referring to FIG. 11, if a small amount of gas exists between two adjacent columnar structures 122, it is easy to form a gas-liquid-solid three-phase system O among the test liquid, the small amount of gas, and the base layer 121 and the columnar structure 122 included in the dielectric layer 120, which makes the hydrophobic performance of the dielectric layer 120 better.

Figure 6:
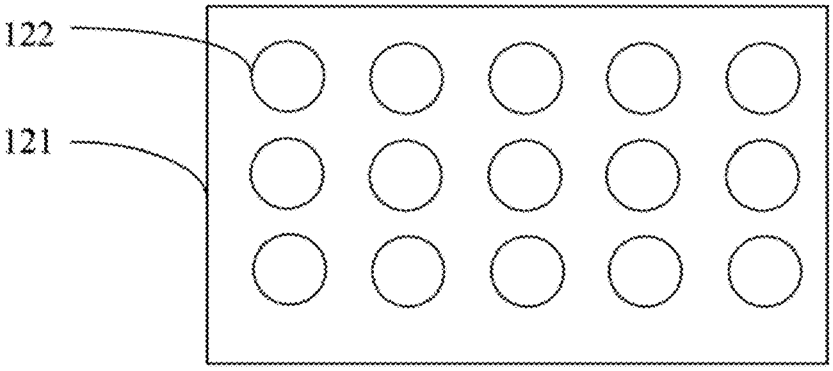
FIG. 6 is a top view of a dielectric layer, in accordance with some embodiments of the present disclosure.
Figure 7:
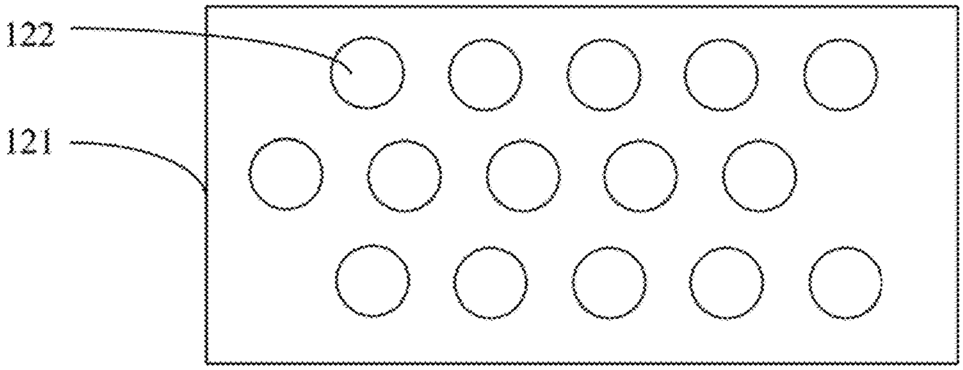
FIG. 7 is a top view of another dielectric layer, in accordance with some embodiments of the present disclosure.
Figure 8:
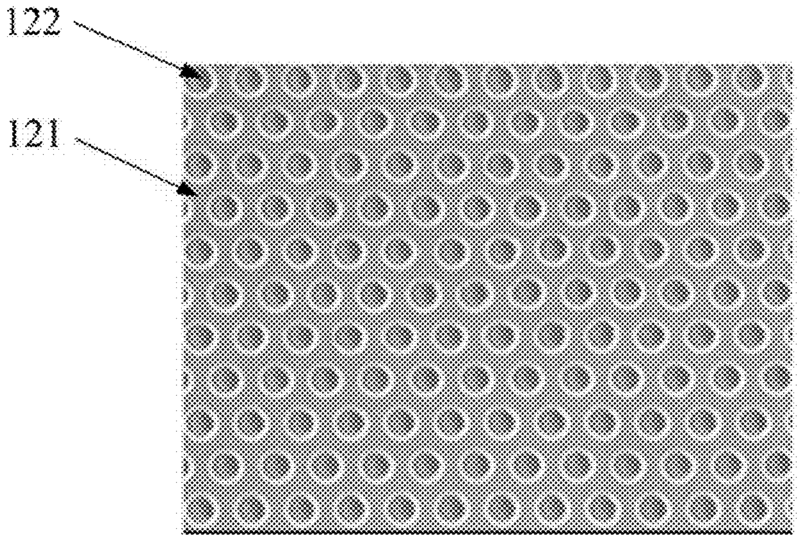
FIG. 8 is an electron micrograph of a dielectric layer, in accordance with some embodiments of the present disclosure.

It will be noted that, as shown in FIGS. 3, 6 and 7, the columnar structure 122 is a columnar structure 122 in a general sense, that is, the columnar structure 122 is a cylindrical structure or a prismatic structure, and is also a conical frustum shaped structure, a pyramidal frustum shaped structure or a special-shaped columnar structure. In a case where the columnar structure 122 is the conical frustum shaped structure or the pyramidal frustum shaped structure, an area of an end face of the columnar structure 122 adjacent to the base layer 121 is greater than an area of an end face of the columnar structure 122 away from the base layer 121, which is conductive to increasing the contact area between the dielectric layer 120 per unit area and the test liquid.

In some embodiments, the plurality of columnar structures 122 are evenly distributed on the surface of the base layer 121. For example, the plurality of columnar structures 122 are arranged in a matrix form as shown in FIG. 6. For another example, the plurality of columnar structures 122 are arranged periodically as shown in FIG. 7. For a perspective of distribution uniformity, the distribution manner may make the hydrophobic performance of portions of the dielectric layer 120 relatively uniform.

In some embodiments, referring to FIGS. 3, 8 and 9, 1×$10^{12}$ to 3×$10^{12}$ columnar structures 122 are formed on the surface of the base layer 121 per square meter. Within this range, a distribution density of the columnar structures 122 is reasonable, and the dielectric layer 120 has good hydrophobic performance. After the dielectric layer 120 is applied to the microfluidic substrate 100, the microfluidic substrate 100 may control the test liquid better. For example, 1.38×$10^{12}$ columnar structures 122 are formed on the surface of the base layer 121 per square meter.

In some embodiments, as shown in FIG. 3, a radial dimension D of each columnar structure 122 is greater than or equal to a distance r between two adjacent columnar structures 122, so that the surface of the base layer 121 is utilized by the columnar structures 122 as much as possible to reduce an unnecessary waste of space. In this way, it may ensured that the columnar structures 122 are distributed on the surface of the base layer 121 as much as possible, thereby further improving the hydrophobic performance of the dielectric layer 120.

Figure 5:
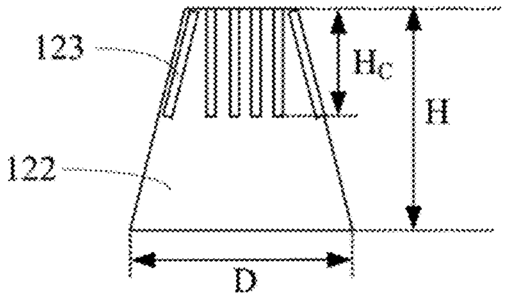
FIG. 5 is a front view of a columnar structure, in accordance with some embodiments of the present disclosure.

In some embodiments, as shown in FIGS. 3, 5 and 11, the radial dimension D of each columnar structure 122 is less than or equal to an axial dimension H of the columnar structure 122, so that a possibility that the small amount of gas exists between two adjacent columnar structures 122 is greater, which is more conducive to forming the gas-liquid-solid three-phase system O to further improve the hydrophobic performance of the dielectric layer 120.

For example, as shown in FIGS. 3 and 5, each columnar structure 122 is the conical frustum shaped structure. An end face of each columnar structure 122 away from the base layer 121 is defined as an upper end face, and an end face of each columnar structure 122 facing the base layer 121 is a lower end face. In this case, a height of each columnar structure 122 (the axial dimension H of the columnar structure 122) is within a range from 1 μm to 5 μm, a diameter of the upper end face is within a range from 0.5 μm to 2 μm, and the distance between two adjacent conical frustums (i.e., the distance r between two adjacent columnar structures) is 0.5 times to 0.8 times the diameter of the upper end face.

In some embodiments, as shown in FIGS. 4, 5, 9 and 10, the dielectric layer 120 further includes a plurality of roughened structures 123. For example, at least one roughened structure 123 of the plurality of roughened structures 123 is provided on a columnar surface of each columnar structure 122, and each roughened structure 123 and the columnar structure 122 where the roughened structure 123 is located may be integrally formed or be separate structures. Moreover, the roughened structure 123 contains the dielectric material as described above. Since the molecular structure of the dielectric material has hydrophobic group(s), the roughened structure 123 has a very low surface energy, so that the roughened structure 123 has good hydrophobicity. Moreover, the roughened structure 123 may increase the specific surface area of the columnar structure 122, so that the contact area between the dielectric layer 120 per unit area and the test liquid is further increased, thereby further improving the hydrophobicity of the dielectric layer 120.

For example, as shown in FIG. 5, multiple roughened structures 123 extend from an end of the columnar structure 122 away from the base layer 121 toward an end of the columnar structure 122 adjacent to the base layer 121, and a dimension Hc of each roughened structure 123 in an axial direction of the columnar structure 122 is less than or equal to the axial dimension H of the columnar structure 122. In this case, the roughened structures 123 are not provided on a whole surface of the columnar structure in the axial direction of the columnar structure, that is, the roughened structures 123 are disposed on a portion of the columnar surface of the columnar structure away from the base layer 121 (i.e., there is a gap between the roughened structures 123 and the base layer 121). In this way, the portion of the columnar surface of the columnar structure away from the base layer 121 has good hydrophobicity, so that the portion of the columnar surface of the columnar structure away from the base layer 121 and the test liquid have a poor contact. Therefore, when the test liquid begins to approach the base layer 121 along the columnar surface of the columnar structure, the portion of the columnar surface of the columnar structure 122 away from the base layer 121 may prevent the test liquid from moving toward the base layer 121 along the columnar surface of the columnar structure 122. In this way, a probability that the test liquid comes into contact with the portion of the columnar surface of the columnar structure 122 proximate to the base layer 121 (i.e., a portion of the columnar surface of the columnar structure 122 on which the roughened structure 123 is not formed) and the surface of the base layer 121 is reduced, thereby further improving the hydrophobicity of the dielectric layer 120.

In addition, as shown in FIGS. 5 and 11, if the small amount of gas exists between two adjacent columnar structures 122, the probability that the test liquid comes into contact with the portion of the columnar surface of the columnar structure 122 proximate to the base layer 121 (i.e., the portion of the columnar surface of the columnar structure 122 on which the roughened structure 123 is not formed) and the surface of the base layer 121 is low, which is conducive to the formation of the gas-liquid-solid three-phase system O.

For example, as shown in FIG. 5, in a case where the dimension Hc of each roughened structure 123 in the axial direction of the columnar structure 122 is less than the axial dimension H of the columnar structure 122, the dimension Hc of the roughened structure 123 in the axial direction of the columnar structure 122 is 0.25 times to 0.5 times the axial dimension H of the columnar structure 122. Within this range, the hydrophobicity of the dielectric layer 120 may be effectively improved.

Figure 4:
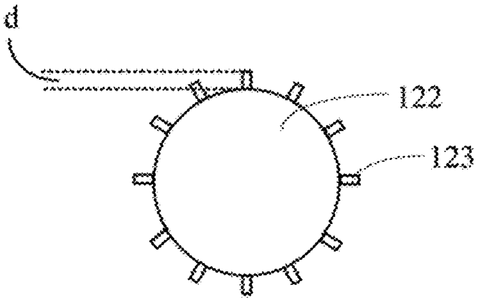
FIG. 4 is a top view of a columnar structure, in accordance with some embodiments of the present disclosure.

For example, as shown in FIGS. 4 and 5, a dimension d of each roughened structure 123 in a radial direction of the columnar structure 122 is 0.06 times to 0.1 times the axial dimension H of the columnar structure 122, so as to prevent a center of gravity of the columnar structure 122 from being affected by the roughened structure 123, which makes the stability of the columnar structure 122 strong. For example, in a case where the axial dimension of the columnar structure 122 is 1 μm to 5 μm, a length of the roughened structure 123 in the radial direction of the columnar structure 122 is 100 nm to 300 nm.

For example, as shown in FIGS. 4, 5, 9 and 10, multiple roughened structures 123 are sequentially formed on the columnar surface of the columnar structure 122 in a circumferential direction of the columnar structure 122. In orthographic projections of each columnar structure 122 and all roughened structure 123 on the columnar surface of columnar structure 122 on the base layer 121, an edge per micrometre of an orthographic projection of an end face of the columnar structure 122 away from the base layer 121 is connected to orthographic projections of 16 to 32 roughened structures. For example, in a case where the orthographic projection of the end face of the columnar structure 122 away from the base layer 121 on the base layer 121 is a circular projection with a diameter of 0.5 μm to 2 μm, the number of the roughened structures 123 is 50 to 100. In this case, each columnar structure 122 does not have a problem of instability of center of gravity due to excessive roughened structures 123 or uneven distribution of roughened structures 123.

For example, the end face of the columnar structure 122 away from the base layer 121 is parallel to the base layer 121, which may better solve the above problem of instability of center of gravity.

Figure 10:
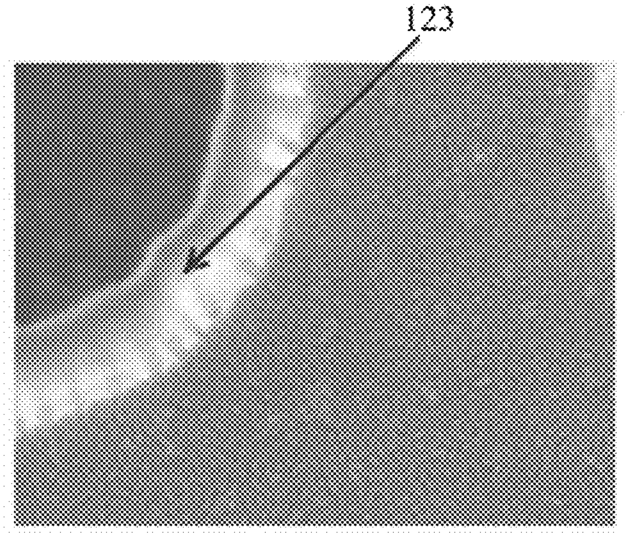
FIG. 10 is an electron micrograph of a roughened structure, in accordance with some embodiments of the present disclosure.

In some embodiments, as shown in FIG. 10, the at least one roughened structure 123 of the plurality of roughened structures is a protrusion disposed on the columnar surface of the columnar structure 122 where the at least one roughened structure 123 is located. It will be noted that a specific form of the protrusion is various. For example, the protrusion may be a tapered structure disposed on the columnar surface of the columnar structure 122, a tip of the tapered structure is away from the columnar surface of the columnar structure 122 in the radial direction of the columnar structure 122, and a bottom of the tapered structure is combined with the columnar surface of the columnar structure 122.

Figure 9:
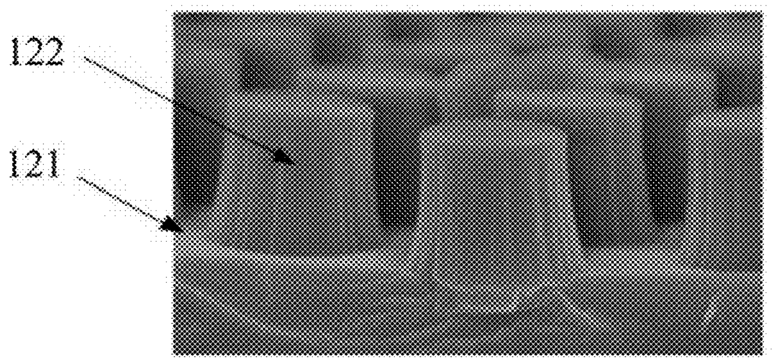
FIG. 9 is an electron micrograph of columnar structures, in accordance with some embodiments of the present disclosure.

In some embodiments, as shown in FIG. 9, the at least one roughened structure 123 of the plurality of roughened structures is a groove disposed in the columnar surface of the columnar structure 122 where the at least one roughened structure 123 is located. It will be noted that a specific form of the groove is various. For example, the groove is formed in the columnar surface of the columnar structure 122, and extends from an end of the columnar surface of the columnar structure 122 away from the base layer 121 toward an end of the columnar surface of the columnar structure 122 adjacent to the base layer 121. For example, a dimension of the groove in the axial direction of the columnar structure 122 is less than the axial dimension of the columnar structure 122, and there is a gap between the groove and the base layer. Specific effects may be referred to the above description of effects of the roughened structure 123.

There are various methods for manufacturing the microfluidic substrate 100. The method for manufacturing the microfluidic substrate 100 provided by some embodiments of the present disclosure will be described below with reference to the accompanying drawings.

Figure 14:
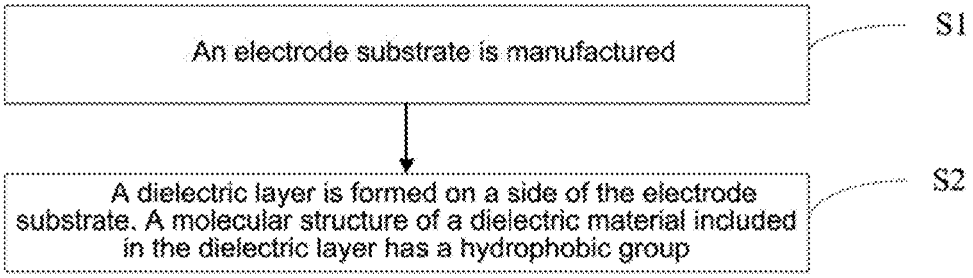
FIG. 14 is a flow chart of a method for manufacturing a microfluidic substrate, in accordance with some embodiments of the present disclosure.

As shown in FIGS. 2, 3 and 14, some embodiments of the present disclosure provide a method for manufacturing a microfluidic substrate 100, and the method for manufacturing the microfluidic substrate 100 includes the following steps.

In S1, an electrode substrate 110 is manufactured.

In S2, a dielectric layer 120 is formed on a side of the electrode substrate 110. A molecular structure of a dielectric material included in the dielectric layer 120 has a hydrophobic group.

In the microfluidic substrate 100 manufactured through the above steps, the dielectric layer 120 has both a dielectric function and a certain hydrophobic function. Therefore, in a process of manufacturing the microfluidic substrate 100, there is no need to form a hydrophobic layer 130 on a surface of the dielectric layer 120 away from the electrode substrate 110, which not only simplifies the structure and manufacturing process of the microfluidic substrate 100, thereby improving production efficiency, but also reduces the probability of a foreign object piercing the dielectric layer 120, thereby improving the production yield of the microfluidic substrate 100.

In addition, since the dielectric layer 120 in the microfluidic substrate 100 has functions of dielectricity and hydrophobicity, the dielectric layer 120 may be used as both a hydrophobic layer and a dielectric layer, so that the problem of poor adhesion between the hydrophobic layer and the dielectric layer included in the existing microfluidic substrate may be solved.

Figure 15:
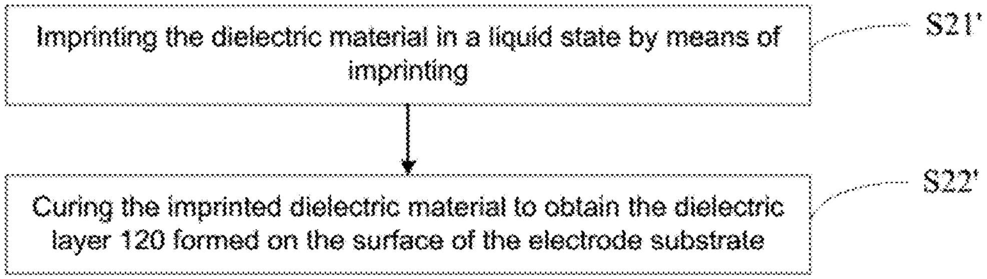
FIG. 15 is a flow chart of a method for manufacturing another microfluidic substrate, in accordance with some embodiments of the present disclosure.

For example, as shown in FIG. 15, the step of forming the dielectric layer 120 includes:

S21', imprinting the dielectric material in a liquid state by means of imprinting; and S22', curing the imprinted dielectric material to obtain the dielectric layer 120 formed on the surface of the electrode substrate 110.

Figure 13:
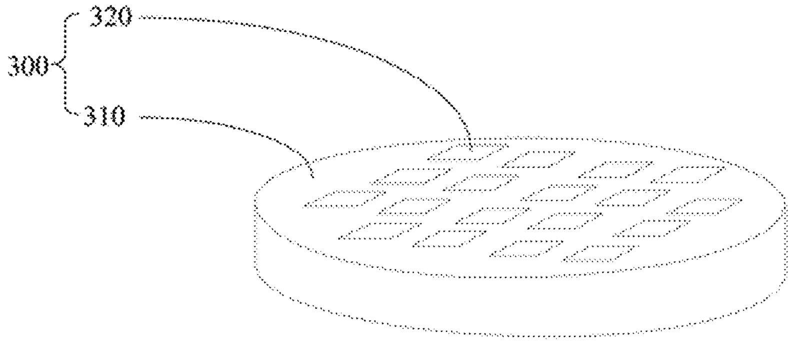
FIG. 13 is a structural diagram of a template, in accordance with some embodiments of the present disclosure.
Figure 16:
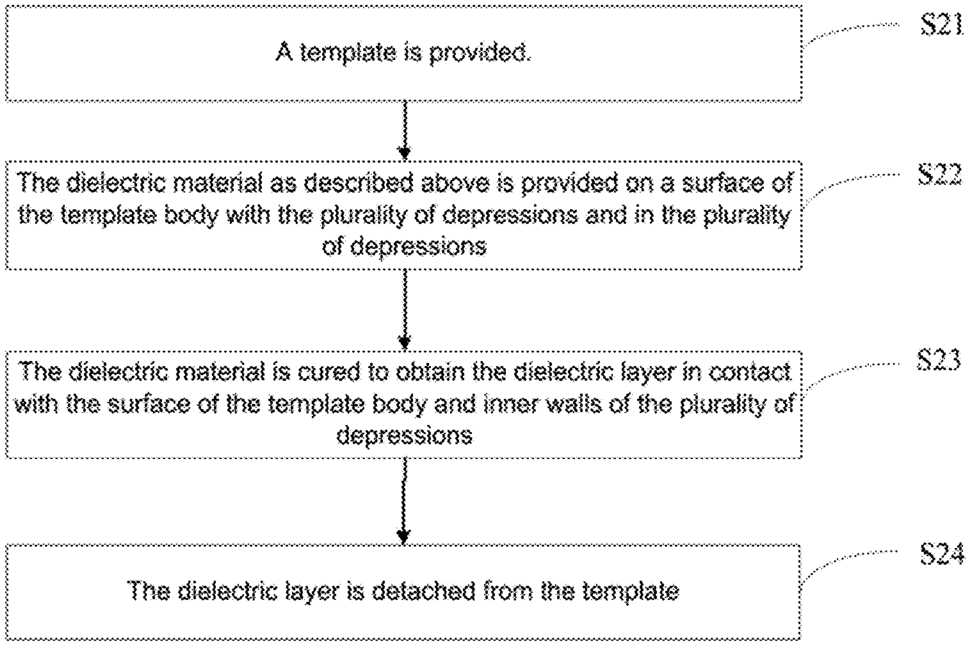
FIG. 16 is a flow chart of a method for manufacturing yet another microfluidic substrate, in accordance with some embodiments of the present disclosure.
Figure 17:
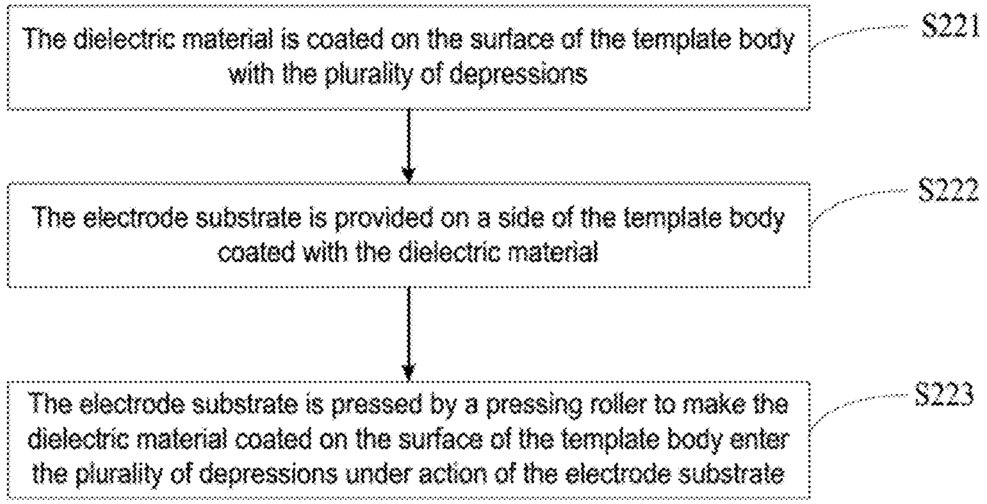
FIG. 17 is a flow chart of a method for manufacturing yet another microfluidic substrate, in accordance with some embodiments of the present disclosure.

In some other embodiments, referring to FIGS. 2 and 3, the dielectric layer 120 includes a base layer 121 and a plurality of columnar structures 122 disposed on a surface of the base layer 121 away from the electrode substrate. In this case, as shown in FIGS. 13 and 16, S2 includes S21 to S24.

In S21, a template 300 is provided. Methods for manufacturing the template 300 are various. For example, the template 300 may be made by electron beam exposure. Referring to FIG. 13, the template 300 includes a template body 310 and a plurality of depressions 320 formed in the template body 310. It can be understood that the plurality of depressions 320 are configured to form the plurality of columnar structures 122 described above. For example, each depression 320 is a microwell structure.

Figure 12:
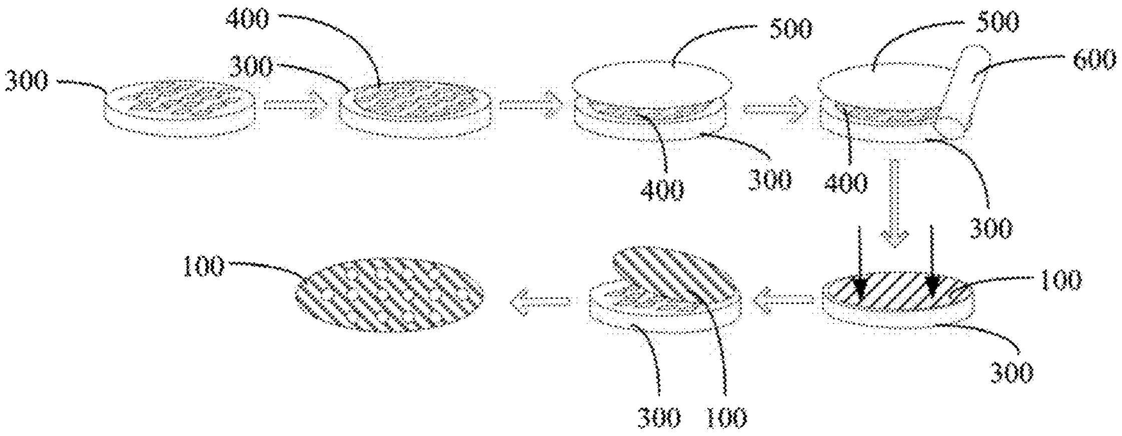
FIG. 12 is a flow chart of manufacturing a dielectric layer, in accordance with some embodiments of the present disclosure.

In S22, the dielectric material 400 as described above is provided on a surface of the template body with the plurality of depressions and in the plurality of depressions. As shown in FIG. 12, it will be noted that the dielectric material 300 is liquid.

In S23, the dielectric material is cured to obtain the dielectric layer in contact with the surface of the template body and inner walls of the plurality of depressions. The curing method may be determined according to properties of the dielectric material 400. For example, in a case where the liquid dielectric material 400 is polydimethylsiloxane, an ultraviolet curing method may be selected as the curing method.

In S24, the dielectric layer is detached from the template.

In the microfluidic substrate 100 manufactured through the above steps, the dielectric layer 120 includes the base layer 121 and the plurality of columnar structures 122 disposed on the surface of the base layer 121 away from the electrode substrate 110. The plurality of columnar structures 122 may increase the contact area between the test liquid and the dielectric layer 120 per unit area. The larger the contact area between the test liquid and the dielectric layer 120 per unit area is, the better the hydrophobic performance of the dielectric layer 120 is. Therefore, the dielectric layer 120 may meet hydrophobic requirements of the microfluidic substrate 100 for the test liquid by controlling the number of the columnar structures 122 disposed on the base layer 121.

For example, as shown in FIGS. 2, 12, 13 and 17, the above S22 includes the following steps.

In S221, the dielectric material is coated on the surface of the template body 310 with the plurality of depressions.

In S222, the electrode substrate 110 is provided on a side of the template body coated with the dielectric material 400. The electrode substrate 110 includes a base substrate 111 and an electrode layer 112 disposed on a side of the base substrate 111, and the electrode layer 112 is in contact with the dielectric material.

In S223, the electrode substrate 110 is pressed by a pressing roller 600 to make the dielectric material 400 coated on the surface of the template body enter the plurality of depressions under action of the electrode substrate 110.

As seen from the above, in a case where the electrode substrate 110 may be used as a separator 500, the electrode substrate 110 may isolate the pressing roller 600 from the dielectric material 400 to prevent contamination of a liquid imprinting material caused by direct contact between the pressing roller 600 and the dielectric material 400. After the dielectric layer 120 that is adhered together with the surface of the template body and the inner walls of the plurality of depressions is obtained, the separator 500 (i.e., the electrode substrate 110) does not need to be removed. The dielectric layer 120 is directly detached from the surface of the template body and the inner walls of the plurality of depressions, and the obtained structure is the microfluidic substrate 100. It will be seen that the manufacturing process of the microfluidic substrate 100 may be simplified in a case where the electrode substrate 110 is used as the separator 500.

Figure 19:
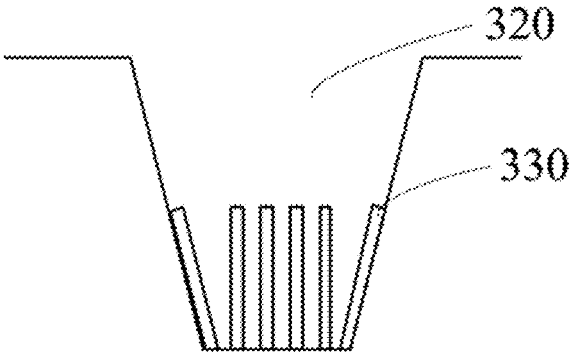
FIG. 19 is a structural diagram of a depression with microstructures, in accordance with some embodiments of the present disclosure.

For example, as shown in FIG. 19, a plurality of microstructures 330 are provided in an inner side wall of at least one depression of the plurality of depressions, and at least one microstructure of the plurality of microstructures is a protrusion (i.e., a protrusion stamper disposed on the inner side wall) or a groove (i.e., a groove tamper disposed on the inner side wall). This design makes the roughened structures 123 be formed on the columnar surface of the formed columnar structure (as shown in FIGS. 4 and 5), and the roughened structures 123 are also made of the dielectric material having hydrophobic group(s), and thus the roughened structures 123 also have good hydrophobicity. Moreover, the roughened structures 123 may also increase the specific surface area of the columnar structure 122, so that the contact area between the dielectric layer 120 per unit area and the test liquid is further increased, thereby further improving the hydrophobicity of the dielectric layer 120.

For example, the plurality of microstructures are sequentially arranged in a circumferential direction of the inner side wall of the depression where the plurality of microstructures are located. This design makes the plurality of roughened structures on the columnar surface of the formed columnar structure be sequentially arranged in the circumferential direction of the columnar structure, so that each columnar structure 122 does not have a problem of instability of center of gravity due to excessive roughened structures 123, and the hydrophobic effect on each side of each columnar structure 122 is similar.

Figure 18:
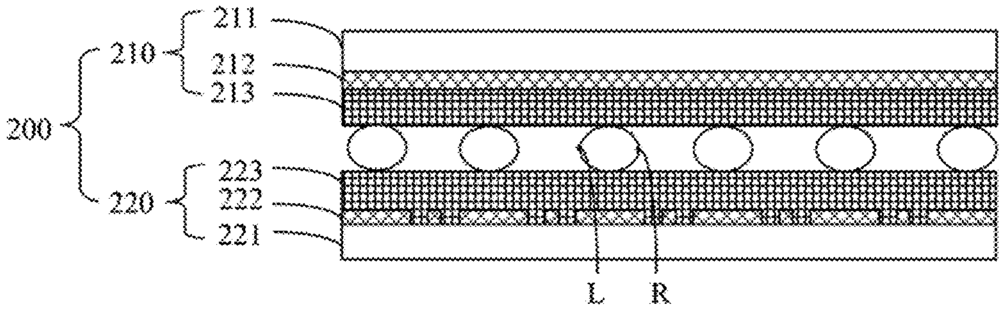
FIG. 18 is a structural diagram of a microfluidic chip, in accordance with some embodiments of the present disclosure.

Some embodiments of the present disclosure provide a microfluidic chip. As shown in FIG. 18, the microfluidic chip 200 includes a first microfluidic substrate 210 and a second microfluidic substrate 220 that are disposed opposite to each other, and at least one of the first microfluidic substrate 210 and the second microfluidic substrate 220 is the microfluidic substrate 100 provided by some embodiments described above. An accommodation space for receiving the test liquid is formed between the first microfluidic substrate 210 and the second microfluidic substrate 220.

The microfluidic chip 200 provided by some embodiments of the present disclosure has all the beneficial effects of the microfluidic substrate described above, which will not be described herein again.

For example, as shown in FIG. 18, the first microfluidic substrate 210 includes a first base substrate 211, a reference electrode layer 212, and a first dielectric layer 213 formed on a surface of the reference electrode layer 212, and the reference electrode layer 212 has a plate shape as a whole. The second microfluidic substrate 220 includes a second base substrate 221, a driving electrode array 222 (i.e., a plurality of driving electrodes arranged in an array), and a second dielectric layer 223 formed on a surface of the driving electrode array 222. An accommodation space for receiving the test liquid is formed between the first dielectric layer 213 and the second dielectric layer 223.

By applying a reference voltage to the reference electrode layer 212, and driving voltages to the plurality of driving electrodes included in the driving electrode array 222, and controlling a magnitude of a voltage of each driving electrode according to actual situations, a left position and a right position of the liquid level of a test droplet (i.e., the test liquid) have different contact angles, thereby controlling the test droplet to roll in the accommodation space between the first microfluidic substrate 210 and the second microfluidic substrate 220. Specifically, for a test droplet, the liquid level of the test droplet is divided into the left liquid level L and the right liquid level R according to orientation, and a contact angle between the test droplet and a surface of the first microfluidic substrate 210 or the second microfluidic substrate 220 is controlled to be reduced by utilizing an input voltage of the driving electrode. Due to hysteresis of a change in the contact angle, the test droplet rolls on the surface of the first microfluidic substrate 210 or the second microfluidic substrate 220. For example, a radius of curvature of a portion of the right liquid level R perpendicular to the first microfluidic substrate 210 or the second microfluidic substrate 220 is increased, and a radius of curvature of a portion of the left liquid level L perpendicular to the first microfluidic substrate 210 or the second microfluidic substrate 220 is unchanged. In this case, the radius of curvature of the portion of the left liquid level L perpendicular to the first microfluidic substrate 210 or the second microfluidic substrate 220 is different from the radius of curvature of the right liquid level R perpendicular to the first microfluidic substrate 210 or the second microfluidic substrate 220, so that an additional pressure of the first microfluidic substrate 210 or the second microfluidic substrate 220 on the right liquid level R is reduced, and an additional pressure of the first microfluidic substrate 210 or the second microfluidic substrate 220 on the left liquid level L is unchanged, which makes the test droplet roll on the surface of the first microfluidic substrate 210 or the second microfluidic substrate 220.

In the description of the above embodiments, specific features, structures, materials or characteristics may be combined in any suitable manner in any one or more embodiments or examples.

The forgoing descriptions are merely specific implementation manners of the present disclosure, but the protection scope of the present disclosure is not limited thereto. Any person skilled in the art could conceive of changes or replacements within the technical scope of the present disclosure, which shall all be included in the protection scope of the present disclosure. Therefore, the protection scope of the present disclosure shall be subject to the protection scope of the claims.

What is claimed is:

1. A microfluidic substrate, comprising:

an electrode substrate; and a dielectric layer disposed on a side of the electrode substrate, the dielectric layer including a dielectric material, and a molecular structure of the dielectric material having a hydrophobic group, wherein the dielectric layer includes:

a base layer; and a plurality of columnar structures disposed on a surface of the base layer away from the electrode substrate, and wherein the base layer and the plurality of columnar structures include the dielectric material only, and the electrode substrate is insulated from the plurality of columnar structures.

2. The microfluidic substrate according to claim 1, wherein the dielectric layer further includes:

a plurality of roughened structures, at least one roughened structure of the plurality of roughened structures is disposed on a columnar surface of each columnar structure of the plurality of columnar structures, wherein the at least one roughened structure extends from an end of the columnar structure away from the base layer toward an end of the columnar structure adjacent to the base layer, and a dimension of the at least one roughened structure in an axial direction of the columnar structure is less than or equal to an axial dimension of the columnar structure.

3. The microfluidic substrate according to claim 2, wherein the dimension of the at least one roughened structure in the axial direction of the columnar structure is 0.25 times to 0.5 times the axial dimension of the columnar structure; and/or, a dimension of the at least one roughened structure in a radial direction of the columnar structure is 0.06 times to 0.1 times a dimension length of the columnar structure.

4. The microfluidic substrate according to claim 2, wherein the at least one roughened structure includes multiple roughened structures, and the multiple roughened structures are arranged in a circumferential direction of the columnar structure where the at least one roughened structure is located.

5. The microfluidic substrate according to claim 4, wherein in orthographic projections of the multiple roughened structures on the base layer and an orthographic projection of the columnar structure where the multiple roughened structures are located on the base layer, an edge per micrometer of an orthographic projection of an end face of the columnar structure away from the base layer is connected to orthographic projections of 16 to 32 roughened structures.

6. The microfluidic substrate according to claim 2, wherein the at least one roughened structure of the plurality of roughened structures is a protrusion disposed on the columnar surface of the columnar structure where the at least one roughened structure is located; and/or the at least one roughened structure of the plurality of roughened structures is a groove disposed in the columnar surface of the columnar structure where the at least one roughened structure is located.

7. The microfluidic substrate according to claim 1, wherein the plurality of columnar structures are arranged in at least one manner of:

the plurality of columnar structures being evenly distributed on a surface of the base layer;

an orthographic projection of the at least one columnar structure of the plurality of columnar structures on the base layer being an orthographic projection at a micron scale;

$1\times10^{12}$ to $3\times10^{12}$ columnar structures being disposed on the surface of the base layer per square meter;

a radial dimension of a columnar structure being greater than or equal to a distance between two adjacent columnar structures;

the radial dimension of the columnar structure being less than or equal to an axial dimension of the columnar structure;

an area of an end face of the columnar structure adjacent to the base layer being greater than or equal to an area of an end face of the columnar structure away from the base layer;

a shape of the columnar structure being a conical frustum shape or a cylinder;

an orthographic projection of the end face of the columnar structure away from the base layer on the base layer being a circular projection; or the end face of the columnar structure away from the base layer being parallel to the base layer.

8. The microfluidic substrate according to claim 1, wherein a thickness of the dielectric layer is d:

$$d=2\gamma_{LG}(\cos\theta-\cos\theta_0)/V^2\varepsilon^0\varepsilon,$$

wherein V is a voltage applied to the electrode substrate, $\varepsilon_0$ is a vacuum dielectric constant, $\varepsilon$ is a dielectric constant of the dielectric material included in the dielectric layer, $\theta_0$ is an initial contact angle of a test liquid on the dielectric layer, $\theta$ is a contact angle of the test liquid on the dielectric layer under action of the applied voltage, and $\gamma_{LG}$ is a surface tension of the test liquid at a gas-liquid interface at 25° C.

9. The microfluidic substrate according to claim 1, wherein a dielectric constant of the dielectric material included in the dielectric layer is 2 to 8.

10. The microfluidic substrate according to claim 1, wherein the dielectric material is selected from the group consisting of polydimethylsiloxane, polymethyl methacrylate, fluorosilicone rubber and mixtures thereof.

11. The microfluidic substrate according to claim 1, wherein the hydrophobic group is selected from the group consisting of an alkyl group, an ester group, a halogen and mixtures thereof.

12. The microfluidic substrate according to claim 1, wherein the electrode substrate includes:

a base substrate; and an electrode layer disposed between the base substrate and the dielectric layer, wherein the electrode layer includes a plurality of driving electrodes arranged in an array, or the electrode layer includes a whole layer of reference electrode.

* * * * *